_United States Patent_ [19]

Braid

[11] 4,443,381

[45] Apr. 17, 1984

[54] DIRECT EXCHANGE PROCESS

[76] Inventor: Milton Braid, 11 MacArthur Blvd., Westmont, N.J. 08108

[21] Appl. No.: 166,662

[22] Filed: Jul. 7, 1980

[51] Int. Cl.$^3$ .................. C10M 1/54; C07F 15/02; C07F 15/04; C10M 3/48
[52] U.S. Cl. .................. 260/439 R; 260/429 K; 260/429 D; 252/42.7; 44/68
[58] Field of Search ............ 260/429 K, 439 R, 125, 260/429 D; 252/42.7; 44/68

[56] References Cited

U.S. PATENT DOCUMENTS

| | | | |
|---|---|---|---|
| 2,249,626 | 7/1941 | Cook et al. | 260/429 D |
| 2,263,445 | 11/1941 | Reiff | 260/429 D |
| 2,270,183 | 1/1942 | Cook et al. | 260/429 D |
| 2,281,401 | 4/1942 | Wilson | 260/429 D |
| 2,342,887 | 2/1944 | Nelson | 260/429 D |
| 2,362,293 | 11/1944 | McNab et al. | 252/42.7 |
| 2,409,687 | 10/1946 | Rogers et al. | 44/76 |
| 3,130,160 | 4/1964 | Morway et al. | 252/42.7 |
| 3,541,014 | 11/1970 | LeSuer | 252/427 |
| 4,119,548 | 10/1978 | Braid | 44/68 |
| 4,198,303 | 4/1980 | Braid | 44/68 |
| 4,211,663 | 7/1980 | Braid | 44/68 |

_Primary Examiner_—Delbert E. Gantz
_Assistant Examiner_—Raymond Covington

[57] ABSTRACT

A direct exchange process wherein compounds are prepared by replacing calcium in neutral and overbased calcium phenol sulfides with transition metals by reaction with transition metal salts in the presence of an accelerator or promoter provides useful stabilizer-detergent additives for lubricating compositions.

17 Claims, No Drawings

DIRECT EXCHANGE PROCESS

BACKGROUND OF THE INVENTION

1. Field of the Invention

This invention is directed to a simplified process of direct interchange for converting calcium derivatives of phenol sulfides to transition metal containing derivatives of phenol sulfides. Such compounds are useful as lubricant oil additives.

2. Discussion of the Prior Art

Calcium derivatives of phenol sulfides are known, are extensively used and are highly useful in the lubricating art. Transition metal derivatives of precursor phenol sulfides have been disclosed in for example U.S. Pat. Nos. 2,409,687 and 2,362,293. Conversion of phenol sulfides to products containing both transition metals and alkaline earth metals by reaction with mixtures of basic salts of those metals have also been disclosed, see the aforementioned U.S. Pat. No. 2,362,293. However, it is believed that the method of preparing transition metal-containing calcium derivatives of phenol sulfides by direct interchange reaction as disclosed herein is not known or disclosed in the prior art. The prior use of mixtures of transition metal basic salts and alkaline earth metal basic salts differs from the process of this invention, inter alia, in that in the prior art the inclusion of the transition metal is random and substantially uncontrolled; the amount of transition metal included is highly variable and significant amounts of unreacted costly transition metal salts are thus wasted or rendered difficult and expensive to recover. Furthermore, the composition of such products is so different from the products of this invention that they have an inability to achieve or carefully control that desired and most effective balance between antioxidation activity, lubricant detergent properties and reserve alkalinity which is readily achieved by said products of the present invention.

SUMMARY OF THE INVENTION

This invention is therefore directed to a novel process of converting calcium derivatives of phenol sulfides to transition metal containing compounds by direct exchange reactions, that is, the reactions take place without reconversion to the original phenol sulfides or alkali metal salts thereof. The degree of conversion can be partial or complete depending upon, inter alia, such factors as reagents, reactant ratios, reaction conditions and reaction times.

It has now been found that calcium, in derivatives of phenol sulfides which may or may not contain excess amounts of calcium, as calcium carbonate, beyond the calculated amount for a neutral salt, may be directly replaced by transition metals such as nickel, cobalt, or iron. The replacement based on the amount of calcium remaining in the product may be total or partial. The degree of replacement depends on the proportion of transition metal reagent, the extent of overbasing of the calcium phenate and choice of reaction media or solvent systems as well as previously mentioned reaction conditions as for example temperature and time.

The method is based primarily on the relative insolubility of the inorganic interchange reaction products such as, for example, calcium sulfate and/or calcium carbonate. A further feature of this development is the use of an interphase agent or interchange promoter or accelerator, such as alcohol, when water or other organic-immiscible phase is used as one member of the solvent system.

This development provides a means of converting a variety of commercially available materials with certain desirable properties to particularly useful lubricant additives, e.g., for stabilization of lubricant compositions against oxidative deterioration. The lubricants thus produced have prolonged and significantly greater effectiveness than that imparted to lubricants by other such additives and the inherent detergent properties of the interchanged reaction products reduce or eliminate the need for additional detergent additives in formulations containing same.

DESCRIPTION OF SPECIFIC EMBODIMENTS

In general the novel process of this invention comprises reacting a transition metal salt with a calcium derivative of a phenol sulfide in an appropriate solvent system to yield the transition metal exchange product. The solvent system may be heterogeneous consisting of an organic phase in which the calcium derivative of the phenol sulfide is soluble, for example process oil, refined petroleum, benzene, xylene, petroleum ether or mixtures thereof and an immiscible phase such as water or methanol in which the transition metal salts have some solubility. Alternatively, both the calcium phenolate sulfide and the transition metal salt such as the sulfate may both be suspended in a solvent in which each has at least some degree of solubility for example isopropyl alcohol. The essential requirements of the solvent system are that the reactants have at least a minimal degree of solubility, that the interchanged product be soluble in one phase of the solvent system and that the displaced calcium salt or salts be insoluble in the system.

The metals preferred are iron, cobalt and nickel. The metal salts generally comprise sulfates, fluosilicates, hypophosphites, or any other suitable salt. Preferred are the iron, cobalt and nickel sulfates.

The alcoholic accelerators generally used are $C_1$ to $C_4$ alcohols which may be primary, secondary or tertiary or mixtures of such alcohols. Preferred are methanol and ethanol or a mixture thereof.

Any suitable calcium phenol sulfide or derivative thereof may be used in the novel process in accordance with this invention. Preferred are the calcium compounds of phenol sulfides derived from para-alkylphenols. Most preferred are the calcium products of phenol sulfides derived from 4-alkylphenols in which the alkyl groups contain from 4 to 16 carbon atoms in any isomeric arrangement with a total of from 4 to 32 carbon atoms the alkylated portions of the phenal sulfides.

The process in general is carried out under ambient conditions of temperature and pressure. However, a temperature range of from about 30° C. to about 125° C. is preferred. Also generally the process is carried out using an excess of the transition metal salt, that is, having an amount of the transition metal present greater than the amount to be incorporated into the exchanged product. The water-soluble transition metal salt not reacted in the exchange process can be conveniently recovered by aqueous extraction from the displaced calcium salts and directly recycled as the aqueous extract.

Having described the invention in general the following detailed and specific material is nonetheless exemplary and not intended in any way to limit the invention.

EXAMPLE 1

A commercial process oil-diluted-overbased calcium alkylated phenol sulfide typically having total base numbers of 140–150 and calcium content of 5.25% which may be manufactured by the catalyzed reaction of the alkylated phenol with sulfur in the presence of basic calcium.

EXAMPLE 2

A commercial process oil-diluted-neutral calcium alkylated phenol sulfide typically having a total base number of about 100 and calcium content of about 3.5% which may be made by reaction of the alkylated phenol with sulfur halide and conversion of the resulting phenol sulfide to the calcium derivative.

EXAMPLE 3

Separation of Diluent Oil from Overbased Calcium Phenol Sulfide

To an aliquot of commercial oil-diluted-overbased (total base number, 140) calcium phenol sulfide (29.4 g) as described in Example 1 stirred magnetically, there was added rapidly at room temperature, 2-propanol (400 ml) which caused the precipitation of solids. After several hours of stirring the precipitated solids were collected and air dried to give 7.2 g which gave the following elemental analysis: C, 55.10%; H, 7.53%; S, 6.70%; Ca, 10.3%.

Additional treatment with 2-propanol (300 ml) afforded a second fraction of 6.9 g of solids with the following elemental analysis: C, 55.29%; H, 7.69%; S, 6.50%; Ca, 9.9%.

Removal of the 2-propanol from the liquid residue left mainly the diluent oil which the infrared spectrum showed to contain phenol and/or phenol sulfide which had not been converted to calcium derivatives in the original processing.

EXAMPLE 4

Nickel Exchanged Overbased Calcium Phenol Sulfide—Effect of Prolonged Reaction Time at Higher Temperature in the Presence of Nickel Sulfate To a clear solution of the commercial overbased (total base number, 140) calcium thiobis(alkylphenate) described in Example 1, an approximately 57% concentrate in diluent oil (183.9 g) in xylene (500 ml), there was added a solution of nickel sulfate hexahydrate (52.5 g) in water while stirring at room temperature. The resulting reaction mixture was heterogeneous but free of solids. Denatured ethanol (50 ml) was added and after a few minutes solids began to precipitate. The temperature of the reaction mixture was raised to 35° C. for 0.5 hr. and then to 80°–90° C. as precipitating solids caused substantial thickening. Additional xylene (200 ml) was added as water was removed by azeotropic distillation during a total 5 hr. reaction period as the temperature rose to 140° C. The resulting mixture was filtered hot and the filtrate was stripped of solvent xylene under reduced pressure. The oil concentrate of the nickel-exchanged product was obtained as a greenish dark brown moderately viscous liquid with the following elemental analysis: S, 3.39%; Ca, 0.51%; Ni, 3.72%.

EXAMPLE 5

Nickel Exchanged Overbased Calcium Phenol Sulfide

To a solution of the commercial overbased alkylated phenol sulfide of Example 1 (183.9 g) in n-heptane (750 ml) there was rapidly added a solution of nickel sulfate hexahydrate (52.5 g) in water (150 ml). The reaction mixture was stirred and heated at reflux until 50 ml of water had been removed. There was only a minor amount of insoluble solids observable in the mixture. To the reaction mixture ethanol (50 ml) was added rapidly which resulted in precipitation of solids and increasing turbidity during a total time of 3.5 hr. At the end of this time the precipitated solids had coagulated mainly in the aqueous phase. The reaction mixture was stripped of solvents and water under reduced pressure. Filtration of the distillation residue afforded the product as a viscous dark amber oil with the following elemental analysis: S, 3.10%; Ni, 3.27%; Ca, 0.98%.

EXAMPLE 6

Nickel Exchanged Overbased Calcium Phenol Sulfide—Effect of Short Time at Low Temperature To a clear solution of the commercial overbased (total base number, 140) calcium thiobis(alkylphenate) of Example 1 comprising an approximately 57% concentrate in refined petroleum oil diluent (183.9 g) in n-heptane containing denatured ethanol (50 ml) there was added rapidly, while stirring, a solution of nickel sulfate hexahydrate (52.5 g) in water (150 ml). Precipitation of solids which began almost at once during the addition continued during the subsequent 1.5 hr. reaction period at room temperature. The reaction mixture was washed with water to remove unreacted nickel sulfate and the solids-containing organic layer was taken up in xylene. The xylene mixture was azeotroped to remove all water and then filtered to remove the calcium salt solids. The filtrate was distilled to remove n-heptane and xylene solvents leaving the nickel exchanged product as a greenish dark brown moderately viscous oil concentrate which gave the following elemental analysis: S, 3.58%; Ca, 1.23%; Ni, 3.23%.

EXAMPLE 7

Nickel Exchanged Oil Free Overbased Calcium Phenol Sulfide

To a solution of oil-free overbased calcium phenol sulfide (72 g) precipitated from a commercial overbased (total base number, 140 in the oil diluted commercial product) calcium phenol sulfide by the general method of Example 4 in benzene (560 ml) there was added a methanolic solution of nickel sulfate hexahydrate decanted from a solution-suspension of the metal salt (40 g) in methanol (350 ml). When about 75 vol. % of the solution had been added precipitation of solids in the reaction mixture began and increased rapidly. All of the remaining solution-suspension was then poured into the reaction mixture, stirring was continued at room temperature for 3 hr. and then the mixture was refluxed for about 2.5 hr. The azeotropic mixture of benzene and methanol was azeotropically distilled from the reaction mixture with replacement of the benzene until all of the methanol had been removed. The reaction mixture was filtered and centrifuged to remove solids and the filtrate was stripped of solvent in a rotary film evaporator under reduced pressure. The partially nickel exchanged product remained as a greenish brown solid with the following elemental analysis: C, 51.00%; H, 7.05%; S, 8.30%; Ni, 9.50%; Ca, 5.1%.

EXAMPLE 8

Iron Exchanged Overbased Calcium Phenol Sulfide

To a clear solution of commercial oil-diluted-overbased (total base number, 140 as supplied) calcium phenol sulfide (183.9 g), as per Example 1, in xylene (500 ml) and denatured ethanol (50 ml), there was added while stirring at 40° C. a solution of ferrous sulfate heptahydrate (55.5 g) in water (60 ml). Solids precipitated as the temperature was raised during 0.25 hr. to 82° C. and held for 2.25 hr. while the mixture became increasingly turbid. The temperature was again raised to remove alcohol and water by azeotropic distillation, recycling the xylene. The resulting dried reaction mixture was filtered hot through filter aid and the solvent was stripped from the filtrate under reduced pressure. The iron exchanged product was obtained as a brown oil (171 g) which had the following elemental analysis: S, 3.40%; Fe, 3.2%; Ca, 0.39%.

EXAMPLE 9

Cobalt Exchanged Overbased Calcium Phenol Sulfide

To a solids free reaction mixture consisting of commercial overbased (total base number, 140 as an oil diluted concentrate) calcium phenol sulfide (183.9 g) as per Example 1 in xylene (500 ml) and cobalt II sulfate hexahydrate (52.5 g) in water (150 ml), there was added rapidly while stirring at room temperature denatured ethanol (50 ml). After nearly 0.25 hr. solids began to precipitate. The temperature was raised to 90° C. during about 0.5 hr. and then raised further during about 4 hr. to 135° C. while alcohol and water were removed by azeotroping. Solids were removed by filtration, and the filtrate was stripped of solvent by rotary film evaporation under reduced pressure. The cobalt exchanged calcium phenol sulfide was obtained as a very dark moderately viscous oil concentrate with the following elemental analysis: S, 3.4%; Co, 4.59%; Ca, 0.13%.

EXAMPLE 10

Nickel Exchanged Neutral Calcium Phenol Sulfide

To a solution of the oil diluted neutral calcium sulfide of Example 2 (1471 g) in isooctane (700 ml) heated and stirred at 40° C. was added ethanol (100 ml) and then nickel sulfate hexahydrate (255.4 g). A total of 150 ml of water was added to the reaction medium and the temperature was raised to 81° C. during 4 hr. of heating and stirring and thereafter maintaining the temperature at 80°–81° C. for an additional 3.5 hr. Water and alcohol were removed by reduced pressure distillation and final purging with a nitrogen stream at 135° C. at atmospheric pressure. Solids were removed by filtration through filter aid assisted by dilution with additional solvent. Solvent was removed from the filtrate by rotary film evaporation under reduced pressure leaving the nickel exchanged calcium phenol sulfide oil concentrate as a dark moderately viscous liquid with the following elemental analysis: C, 79.09%; H, 10.98%; S, 1.67%; Ni, 1.16%; Ca, 0.46%.

TABLE

Catalytic Oxidation Test, Refined Petroleum Oil, 325° F., 40 Hours

| Test Oil | Concentration of Additive, Wt. % | ΔNN | ΔKV, % |
| --- | --- | --- | --- |
| Base Oil, no additive | — | 17 | 334 |
| Base Oil + additive of Example 1 | 1 | 12.4 | 224 |
| Base Oil + additive of Example 2 | 2 | 14.7 | 168 |
| Base Oil + additive of Example 3[1] | 1 | 5.8 | 53 |
| Base Oil + additive of Example 4 | 1 | 4 | 13 |
| Base Oil + additive of Example 5 | 1 | 5.6 | 24 |
| Base Oil + additive of Example 6 | 1 | 6.1 | 50 |
| Base Oil + additive of Example 7[1] | 1 | 0.75 | 10 |
| Base Oil + additive of Example 8 | 1 | 3.5 | 20 |
| Base Oil + additive of Example 9 | 1 | 6.8 | 52 |
| Base Oil + additive of Example 10 | 2 | 6.0 | 24 |

[1]Free of diluent oil

The effect on the usefulness of the calcium phenates as oxidation stability improvers can readily be seen by comparing the transition metal interchanged products of this process with the original calcium phenates from which they were derived.

The transition metal interchanged products were tested in a catalytic oxidation test in which the stabilizer agent in solution in a neutral solvent refined base oil having a viscosity at 100° F. of 130 SUS is subjected to heating at 325° F. in the presence of lead, iron, copper, and aluminum metal specimens for 40 hr. while air is passed through at a rate of 5 liters per hour. The extent of oxidative deterioration is assessed by the increase in acidity, change in the neutralization number (ΔNN) as measured by ASTM D-974 and by the observed increase in viscosity (percentage change, %ΔKV). In general, the degree of control of viscosity increase is the more important observation since it reflects more directly the extent to which the functional integrity and stability of a lubricant is maintained. As can be seen from the results of these tests in the Table, the transition metal-containing products of this process are clearly superior to the prior art calcium-containing phenates. Moreover, the degree of oxidative stabilization increases as the residual calcium content decreases.

The above exemplary matter is merely illustrative of the facile and highly efficient process of preparing the novel compounds of this invention. However, it is particularly noteworthy to compare the tests results of Examples 4, 5, 6, 8 and 9 with those of Example 1 and the results of Example 7 with those of Example 3 and the results of Example 10 with those of Example 7. It is clearly obvious from such comparison that the formulations in accordance with the present invention are highly and most unexpectedly superior to the prior art formulations. It is also to be noted as readily understood by those of skill in the art that departures and variations within the scope of this invention can be made.

I claim:

1. A process of preparing transition metal-containing derivative reaction products of calcium phenol sulfides which comprises reaction of said sulfides with a transition metal salt in a multi-phase solvent system in the presence of an alcoholic reaction accelerator or promoter, said solvent system being characterized by having a minimal degree of solubility for said reactants and wherein said reaction products are soluble in at least one phase of said solvent system and the displaced calcium salt produced by said reaction is insoluble in said solvent system.

2. The process of claim 1 wherein the reaction accelerator or promoter is selected from $C_1$–$C_4$ alcohols which may be primary, secondary or tertiary.

3. The process of claim 2 wherein said accelerator is selected from methanol, ethanol, proponal, isopropanol or mixtures thereof.

4. The process of claim 1 wherein the temperature may range from about 30° to 125° C.

5. The process of claim 1 wherein the transition metal salt is a salt selected from the group consisting of cobalt, iron and nickel salts.

6. The process of claim 5 wherein the transition metal salt is nickel salt.

7. The process of claim 5 wherein the transition metal salt is a cobalt salt.

8. The process of claim 5 wherein the transition metal salt is an iron salt.

9. The process of claim 6 wherein the transition metal salt is nickel sulfate.

10. The process of claim 7 wherein the transition metal salt is cobalt sulfate.

11. The process of claim 8 wherein the transition metal salt is iron sulfate.

12. The process of claims 9, 10, or 11 wherein the accelerator or promoter is a mixture of methanol and ethanol.

13. The process of claim 12 wherein the accelerator or promoter is methanol.

14. The process of claim 12 wherein the accelerator or promoter is ethanol.

15. The process of claim 12 wherein the accelerator or promoter is isopropanol.

16. The process of claim 1 wherein the calcium phenol sulfide is derived from an oil diluted calcium phenate comprising alkylphenol sulfides having 4 to 16 carbon atoms in any isometric arrangement; said calcium phenol sulfide having a total of 4 to 32 carbon atoms in the alkylated portions thereof.

17. The process of claim 16 wherein the alcoholic accelerator or promoter is a mixture of methanol ethanol, propanol or isopropanol.

* * * * *

UNITED STATES PATENT AND TRADEMARK OFFICE
CERTIFICATE OF CORRECTION

PATENT NO. : 4,443,381
DATED : April 17, 1984
INVENTOR(S) : Milton Braid

It is certified that error appears in the above-identified patent and that said Letters Patent is hereby corrected as shown below:

On the title page insert --/73/ Assignee: Mobil Oil Corporation, New York, N. Y. --.

Before Item /57/ insert -- Attorney, Agent, or Firm

Alexander J. McKillop

Michael G. Gilman and

Howard M. Flournoy --.

Signed and Sealed this

Twenty-third Day of October 1984

[SEAL]

Attest:

Attesting Officer

GERALD J. MOSSINGHOFF

Commissioner of Patents and Trademarks